United States Patent [19]

Cresswell et al.

[11] 3,998,814
[45] * Dec. 21, 1976

[54] PROCESS FOR PREPARING β-AMINO-α-BENZYLACRYLONITRILES

[75] Inventors: Ronald M. Cresswell, Scarsdale; Russell L. Seaman, Chappaqua, all of N.Y.; 105, 84, 16,606, 01

[73] Assignee: Burroughs Wellcome Co., Research Triangle Park, N.C.

[ * ] Notice: The portion of the term of this patent subsequent to Apr. 13, 1993, has been disclaimed.

[22] Filed: May 2, 1974

[21] Appl. No.: 466,476

Related U.S. Application Data

[60] Continuation of Ser. No. 263,174, June 15, 1972, abandoned, which is a division of Ser. No. 16,606, March 4, 1970, Pat. No. 3,697,512.

[30] Foreign Application Priority Data

| Mar. 6, 1969 | United Kingdom | 11908/69 |
| Mar. 6, 1969 | United Kingdom | 11909/69 |
| May 16, 1969 | United Kingdom | 25171/69 |
| June 13, 1969 | United Kingdom | 30247/69 |

[52] U.S. Cl. ............... 260/240 R; 260/465 E
[51] Int. Cl.² ............ C07D 295/14; C07C 120/00
[58] Field of Search ............ 260/465 E, 247.7 Z, 260/247, 240 K, 240 R

[56] References Cited
FOREIGN PATENTS OR APPLICATIONS
957,797  5/1964  United Kingdom

OTHER PUBLICATIONS

Henshall et al., J. Chem. Soc. 1962, pp. 3040–3043 (1962).
Yanovskaya et al., Tetrahedron, 24, pp. 4677–4688, (1968).
Allinger *Organic Chemistry*, pp. 246–253, (1972).

*Primary Examiner*—Anton H. Sutto
*Assistant Examiner*—Michael Shippen
*Attorney, Agent, or Firm*—Donald Brown

[57] ABSTRACT

Compounds comprising selected N-substituted β-amino-α-benzyl-acrylonitriles and methods of preparing said compounds substantially free from the corresponding benzalacrylonitrile.

The compounds are useful as intermediates in the preparation of antibacterial and antimalarial agents.

10 Claims, No Drawings

PROCESS FOR PREPARING β-AMINO-α-BENZYLACRYLONITRILES

This is a continuation of application Ser. No. 263,174, filed on June 15, 1972, now abandoned, which is a division of Ser. No. 16,606 filed Mar. 4, 1970, now U.S. Pat. No. 3,697,512.

This invention relates to improved methods of preparing 5-benzylpyrimidines and more particularly is related to a class of stable α-benzylacrylonitrile intermediates, and to methods of making such compounds.

2,4,-Diamino-5-benzylpyrimidines possess both antimalarial and antibacterial activities (*J. Am. Chem. Soc.*, 1951, 73, 3758). Maximal antibacterial activity is found among derivatives which bear electron donating substituents in the benzene nucleus and are unsubstituted in the 6th position of the pyrimidine moiety. 2,4-Diamino-5-(3',4',5'-trimethoxybenzyl) pyrimidine or trimethoprim (U.S. Pat. No. 2,909,522) has a moderately broad antibacterial spectrum which includes many of the Gram-positive species but it is also active against species of the genus Proteus. In common with other 2,4-diaminopyrimidines it is a competitor of folic and folinic acids in microorganisms which require these nutrilites, and it can be shown to inhibit dihydrofolate reductase in *Streptococcus faecalis*. A strong potentiative effect is observed when the drug is administered in combination with sulphonamides as a consequence of the sequential blockade of the biochemical pathway which leads to the de novo synthesis of coenzymes F. This potentiation may be demonstrated both in vitro and in experimental infections in mice with Staphyloccoccus and Proteus species.

2,4-Diamino-5-benzylpyrimidines, which includes trimethoprim and 2,4-diamino-5-(3',4'-dimethoxybenzyl)pyrimidine or diaveridine and 2,4-diamino-5-(3',-4'-dimethoxy-5-bromobenzyl)pyrimidine (U.S. Pat. No. 2,658,897), may be administered orally at a dose of 1 mg/kg to 30 mg/kg per day.

Preferably these compounds are administered in tablet form to a mammal being treated, and trimethoprim may advantageously be combined with sulphamethoxazole against certain respiratory infections. A further example of this class is 2,4-diamino-5-(2'-methyl-4',5'-dimethoxybenzyl)pyrimidine (ormetoprim), which has been reported to show antibacterial acitivity, and also has coccidiostatic properties when combined with sulphadimethoxine.

A new route was developed some years ago for the preparation of 2,4-diamino-5-benzylpyrimidines (see Stenbuck, Baltzly and Hood, *J. Org. Chem.*, 1963, 28, 1983 and British Patent Specification No. 957,797). This route comprises the steps of (i) condensing an aromatic aldehyde with a β-substituted propionitrile in the presence of both an alcohol as solvent and a strong base to give a mixture of isomers of formulae (Ia) and (Ib) respectively:

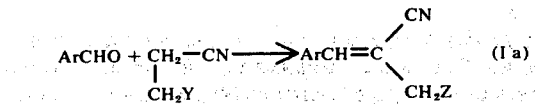

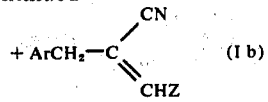

wherein Ar is an optionally substituted phenyl group, Y is an alkoxy, thioalkyl or dialkylamino group, and Z is the group Y or is an alkoxy group derived from the solvent alcohol; and (ii) reacting either the pure 'benzal' isomer (Ia) or a mixture of 'benzal' and 'benzyl' isomers (Ia) and (Ib) respectively with guanidine to give a 5-benzylpyrimidine of formula

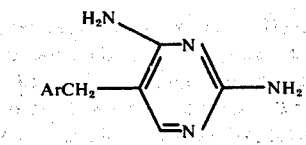

Although it was known that the intermediate product obtained in the first step was a mixture of isomers of formulae (Ia) and (b), only the (Ia) 'benzal' isomer could be isolated in a crystalline form after some purification steps. The two isomers were assumed to be in equilibrium with each other when prepared under alkaline conditions and further reacted with guanidine according to the aforesaid disclosures, but it was not clearly established which of the isomers was primarily interacting in the second step. In many cases this mehtod affords acceptable yields but in certain instances extensive losses (up to about half the material used) ensue from formation of yellow polymers.

The further conversion of composite mixtures of derivatives and isomers according to British Patent Specification No. 957,797, afforded the required 2,4-diamino-5-benzylpyrimidines only is yields between 25 and 45%, and in view of the importance of the final products and the difficulties with by-products and impurities, alternative methods were also explored by various investigators. For instance, the specification of South African Patent Application No. 65/5794 discloses a process comprising the steps of (a) reacting acetylthymine with N-bromosuccinimide to form a acetylbromothymine, (b) condensing the product with a substituted benzene, (c) reacting the product with a halogenating agent, and (d) aminating the halogeno derivative. However, this process suffers from the disadvantages that acetylbromothymine is expensive to make, condensation with the benzene compound does not provide the further intermediate in a high yield, and the last stage requires operation under pressure and usually results in an equilibrium state with consequent poor yields. Altogether the process requires four stages to obtain the final product, and none of the stages is particularly advantageous.

Subsequent developments showed that the polymer formation obtained when operating the process described in the specification of British Pat. No. 957,797, could be prevented or reduced in cases of β-alkoxy-derivatives of compounds (Ia) and (Ib) by temporarily saturating the double bond with excess alkoxide in alcohol.

This provides the corresponding acetal of formula (II), for instance, according to the reaction outlined below:

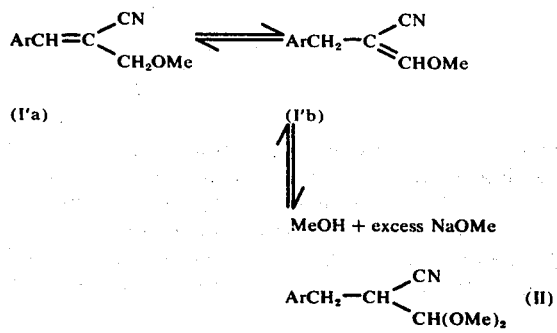

(I'a) (I'b)

MeOH + excess NaOMe $$ArCH_2—CH\underset{CH(OMe)_2}{\overset{CN}{\diagup}} \quad (II)$$

When the acetal (II) is subsequently treated with guanidine in alcoholic solution, the alkaline condition is thought to catalyse the reconsititution of the double bond, initially in the form of (I'b), and the intermediate can thus react with guanidine to give the desired 5-benzylpyrimidine.

Acetals of formula (II) may also be prepared by condensing the corresponding aromatic aldehyde with a 3,3-dialkoxypropionitrile and reducing, preferably catalytically, the 3,3-dialkoxy-2-benzalpropionitrile intermediate so obtained. (See U.S. Pat. No. 3,487,083).

The aforesaid British Patent Specification No. 957,797 also describes (Example 14) the reaction of veratraldehyde with β-dimethylaminopropionitrile in the presence of sodium in ethanol to give a mixture of β-dimethylaminoveratralnitrile (III) and β-ethoxyveratralnitrile (IV) in a 32% yield.

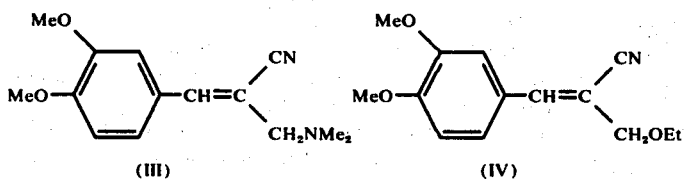

(III) (IV)

It is stated in the Example that this mixture was subsequently cyclised with guanidine to give 2,4-diamino-5-(3',4'-dimethoxybenzyl)-pyrimidine. It is to be noted that both the compounds (III) and (IV) above are 'benzal' derivatives.

It has now been found that N-substituted β-amino-α-benzylacrylonitriles of the configuration of formula (V)

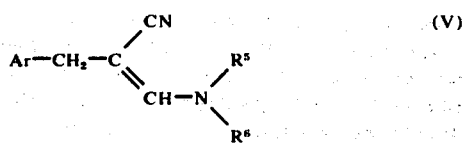

can be prepared remarkably readily under a conveniently wide variety of conditions and that the products so obtained are not only substantially free of contamination with the corresponding 'benzal' isomer but manifest an unexpected stability and capability of maintaining their configuration.

The 'benzyl' configuration of these compounds shows little or no tendency to isomerise into the 'benzal' form prepared and exemplified in the British Patent Specification No. 957,797. Furthermore, the β-amino-αbenzylacrylonitriles can be converted into benzylpyrimidines or into other benzyl derivatives, which may be used as preferred for the preparation of benzylpyrimidines or other heterocyclic ring systems.

According to the present invention in one aspect therefore there is provided an N-substituted-β-amino-α-benzylacrylonitrile compound of the formula (V), in a form substantially free from contamination with the β-amino-α-benzylidenepropionitrile isomer. In particular the contamination with the 'benzal' isomer is normally substantially below 10%, taken as a percentage of the amount of compound of formula (V), and preferably below 5 or, still better, below 2%. Usually the best methods for making the compound of formula (V) provide the product with less than 0.5% contamination and frequently no benzal isomer can be detected at all with analytical methods sensitive to even as low as 0.33% admixture. It has, on the other hand, been observed that contamination at or above the 10% level adversely affects the yield and quality of the final benzylpyrimidine product, and the appearance of purple or yellow discolourisation may aggravate the difficulties, especially isolation in a pure form, an essential requirement when the product is to be used clinically, there therefore being necessary many tedious, time-consuming and accordingly expensive purification steps.

As previously defined Ar is an optionally substituted phenyl group in formula (V). The β-amino group $Nr^5R^6$ is an aliphatic, heterocyclic or aromatic amino group, and can have only one hydrogen atom for $R^5$ and $R^6$. In general it may be stated that, as a free amine, $HNR^5R^6$ is preferred to have a Pka value not lower than about 0, and also most preferably not higher than about 6.

In particular, it is especially preferred that the $NR^5R^6$ group is a primary anilino group (e.g. aniline, o and p -toluidine p-anisidine,p-chloroaniline, 2,5 and 3,4 - dichloroanilines). The phenyl ring of this group may be optionally substituted with one or more substituents such as halogen atoms, and alkyl and alkoxy groups, but the unsubstituted anilino group is, however, particularly preferred.

The $NR^5R^6$ group may also be a primary amino group other than the aforesaid primary anilino group, such as a monoalkylamino, benzylamino, or naphthylamino, preferably α-β-naphthylamino group; or may be a secondary amino group, such as a dialkylamino,N-ethylanilino,pyrrolidino, piperidino, N-methylanilino or a piperazino group, or most preferably the morpholino group.

In particular the invention provides compounds of formula (VIII), in a form substantially free from contamination with the β-amino-4-benzylidene-propionitrile isomer, as hereinbefore defined:

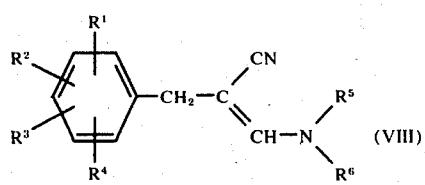

(VIII)

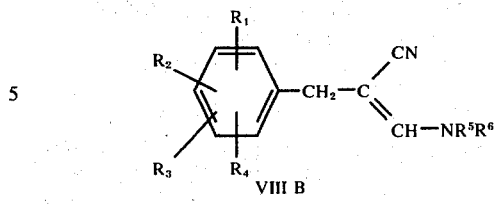

VIII B wherein the group —NR$^5$R$^6$ is as hereinbefore defined with reference to a compound of formula (V), and R$^1$, R$^2$, R$^3$ and R$^4$ are the same or different and each is a hydrogen or a halogen atom, an alkyl, alkoxy, or benzyloxy group, or R$^3$ and R$^4$ taken together may be a methylendioxy group when both R$^1$ and R$^2$ are hydrogen atoms. Preferably the whole amino group Nr$^5$R$^6$ comprises not more than 12 carbon atoms.

All of the above compounds of formula VIII are convertible to benzyl pyrimidines and such pyrimidines are useful as antibacterials.

In formulae (V) and (VIII), and elsewhere in this application each of the alkyl or alkoxy groups in the substituents may have from 1 to 4 carbon atoms, e.g. they may be methyl, ehtyl, propyl or butyl groups, including normal, iso or tertiary branched forms, and corresponding alkoxy groups. Each of the halogen atoms may be represented by a chlorine, bromine, fluorine or iodine atom.

More particularly the para-position of the phenyl group may be substituted with a benzyloxy, but preferably an alkoxy group, such as a methoxy group, especially with a similar or identical alkoxy substitution at one or advantageously both adjacent positions on the phenyl ring. As another possibility alkoxy, e.g. methoxy substitution, in such positions may be combined with an alkyl, e.g. methyl, substitution at the ortho-position of the phenyl group.

The compounds of formulae V (or VIII) fall into two classes A and B dependent on their reactivity towards guanidine.

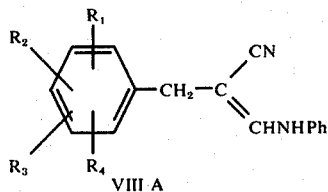

VIII A

Wherein Ph is an aryl group of 6 to 12 carbon atoms which may be substituted in one, two, or three positions with lower alkyl, lower alkoxyl, and halogen, preferably chlorine and where the R$_1$–R$_4$ are defined as previously and lower alkyl halogen and lower alkoxyl are as previously defined. Compounds of type VIII A react readily with guanidine in e.g. solvent lower alcohol solution to form 2,4-diamino-5-benzylpyrimidines in good yield. Advantageously the reaction is conducted at the reflux temperature of the solution, but useful rates are found at lower temperatures down room temperatures. These compounds are consequently preferred.

The compounds of formula VIII wherein R$_5$ is alkyl or aryl and R$^6$ is alkyl and may also be hydrogen when R$_5$ is alkyl and Nr$_5$–R$_6$ may also be cyclic amino such as morpholino, piperidino and pyrrolidino, react only slowly with guanidine base, so that periods of 1–2 weeks would be required for complete reaction. They can be converted to pyrimidines by reaction with guanidine carbonate in a polar aprotic solvent (as defined below but preferably DMSO) at an elevated temperature. This reaction is slow below 140° C but goes rapidly at about 160° C or above.

The compounds according to formula (V) or (VIII), respectively, may be prepared by a wide variety of methods. The actual choice between these methods in any particular instance depends primarily on the reactivity of the compound obtained, and the further processing to which it may be subjected to provide compounds such as pyrimidines of clinical utility, the further processing being itself governed to a great extent by the nature of the amino group Nr$^5$R$^6$, this acting as a leaving group in the further reactions.

Compounds according to formula (V) or (VIII) can be prepared by a method provided by the present invention, which comprises reacting the corresponding benzaldehyde with the corresponding β-aminopropionitrile in the presence of a base in a polar aprotic solvent compatible with and dissolving both reactants.

Polar aprotic solvents suitable for the purpose include hexamethylphosphoramide and N,N-dimethylacetamide, but best results have been obtained with dimethylsulphoxide as the solvent. Bases required for the reaction include the hydroxide, the alkoxides especially the lower alkoxides, preferably the methoxide or tert.-butoxide anions, and the methylsulphinyl carbanion, used in association with a suitable cation, such as an alkali metal (e.g. sodium or potassium or a quaternary ammonium cation (e.g. N-benzyl-N,N,N-trimethylammonium).

Advantageously, the amount of base can be considerably reduced to "catalytic amounts", i.e. effective quantities of less than about 0.3 molar equivalent calculated on the aldehyde used, particularly at temperatures above 60° C, preferably between 90° C and 130° C. For instance, very good yields have been obtained in this manner using dimethylsulphoxide as the solvent.

Very satisfactory yields have also been obtained, for instance, with β-primary anilino-sustituted compounds with 0.5 to 2 molar equivalents of the base at room (about 20° C) or slightly elevated temperature up to about 60° C in the solvent. Dimethylsulphoxide may be replaced under these conditions as well as by other polar aprotic solvents, expecially hexamethylphosphoramide. It has been found most advantageous to use t-butoxide as the base in the form of the potassium salt in dimethylsulphoxide for the preparation of β-anilino-substituted compounds whilst, for instance, the β-morpholino-analogue may be preferred to be formed in the presence of sodium methoxide in the same medium.

Yet further methods provided by the present invention may be used to obtain selected or preferred ranges of compounds within the scope of formula (V) or (VIII). Accordingly, a method is provided for preparing such compounds, wherein the β-amino group Nr⁵R⁶ is a primary anilino group optionally substituted in the phenyl ring, as hereinbefore defined, which comprises reacting the corresponding benzaldehyde with the corresponding β-primary-anilino-propionitrile. Preferably the reaction is carried out in a polar non-aprotic solvent compatible with and dissolving the reactants in the presence of a base. Conveniently an alkanol may be used for the purpose, and the reaction is desirably carried out at elevated temperatures, say between 40° and 80° C. The preferred alkanol is methanol, particularly when the reactant benzaldehyde is substituted with one or more methoxy groups, since it is possible for exchange to take place between the solvent and the substituents. Bases already listed in relation to the other preparatory methods are again applicable, and may, for instance, be used in a quantity molar equivalent calculated on the aldehyde, especially when the reaction is carried out at the lower end of the indicated temperature range.

Compounds according to formula (V) or (VIII) can also be prepared by reacting the corresponding β-hydroxy-β-phenethylmethylsulphone or sulphoxide with the corresponding β-amino-propionitrile. Very preferably the reactions carried out in the presence of a base in a polar non-aqueous solvent compatible with and dissolving both reactants of elevated temperature above 30° C. The solvent may be an alkanol, such as methanol, ethanol or isopropanol, or most conveniently a polar aprotic solvent such as exemplified above. The base is preferably sufficiently strong on its own for a significant amount of the sulphone or sulphoxide reactant to be converted into the anionic form. Again hydroxides or alkoxides, preferably methoxide or t-butoxide, in the form of an alkali metal salt, have been found very convenient for the purpose. The method is especially suitable for making Type VIII A.

The required β-hydroxy-β-phenethyl-methylsulphone or sulphoxide for the above method, may conveniently be provided by a process described in the provisional specification of British Patent Application No. 25171/69. This process comprises the steps of reacting an appropriately substituted benzoic acid ester with dimethyl sulphone or dimethyl sulphoxide preferably in the presence of a base, and selectively reducing the so obtained acetophenone methylsulphone or methylsulphinyl derivative, for instance, with a suitable reducing agent e.g. (borohydride or with aluminium isopropoxide).

The above defined group of β-primary-anilino-α-benzylacrylonitriles can also be prepared by a method which comprises reacting the corresponding aniline, generally in the form of an acid addition salt, with a compound of formula (V) or (VIII) carrying an amino substituent which has, as the free amine HNR⁵R⁶, a pKa value higher by at least about 3 to 4 units than that of the aniline used for reaction. For instance, a morpholino substituent may, in this manner, be directly replaced by an anilino substituent, morpholine having a pKa value of about 8.6 and the aniline generally about 4 to 5. Preferably the reaction is carried in a polar non-aqueous solvent system, for instance, ethanol or glacial acetic acid, at reflux temperatures.

The compounds VIII A are also preparable by reaction of PhNH₂ with β-hydroxy-α-benzylacrylonitriles:

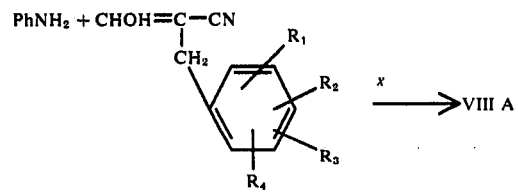

This reaction is conveniently carried out in an organic solvent such as benzene or a lower alcohol or without solvent and where Ph is as previously defined or PhNH₂ could also be Nr⁵R⁶ where this is as previously defined.

The β-hydroxy-α-benzylacrylonitriles are prepared in exemplary fashion by acidification of a partly aqueous solution of a compound of type VIII B wherein R₅ and R₆ are not aromatic. For this variation in aqueous alcohol VIII B is converted to the hydroxy compound X almost instantaneously and in nearly quantitative yield.

The product may then be extracted with an organic solvent from the aqueous medium and reacted with a different amine to obtain a compound according to formula (V) or (VIII). There is little or no tendency to isomerize to the 'benzal' form during these manipulations.

Such a conversion from one amino derivative to another may be achieved in a very high yield, in many instances above 90% in both steps, and the product so obtained can be reacted to form other materials such as benzylpyrimidines in a quality and yield often even better than that provided by using the original β-amino-derivative.

In addition, this method may be very advantageous for preparing certain β-amino-α-benzylacrylonitriles, especially in cases where the Nr⁵R⁶ group is basic but only weakly basic anilino group, e.g. -chloro-anilino. In such instances, there are sometimes difficulties in preparing the corresponding β-anilino-propionionitrile for reaction with the benzaldehyde.

The β-hydroxy-α-benzylacrylonitriles may also be used as intermediates for further syntheses, and can, for instance, be alkylated to provide the appropriate β-alkoxy-α-benzylacrylonitrile, substantially free from the 'benzal' isomer or acetal. The benzyl compound so formed and in such purity is also eminently suitable as a starting material for the synthesis of benzylpyrimidines, and provides the latter in a substantially increased yield and at a better quality than the mixture of benzyl and benzal isomers, or the benzal isomer alone, of the method described in British Patent Specification No. 957,797.

Compounds according to formula (V) or (VIII), wherein the β-amino group Nr⁵R⁶ is a primary amino group other than anilino, or is a secondary amino group, can also be prepared according to the present invention by reacting the corresponding β-alkoxy-α-benzylidenepropionitrile with an excess of the appropriate amine in the presence of a base in an alkanol. Suitable bases are again those already listed for other methods. Preferably the base is the alkoxide corresponding to the solvent. For instance, a β-methoxide-α-benzylidenepropionitrile may be so converted with morpholine, in methanol containing sodium methoxide, to the corresponding β-morpholino-α-benzylacrylonitrile.

The above group of compounds according to formula (V) or (VIII), wherein the β-amino-group NR⁵R⁶ is other than the anilino group, can moreover be prepared according to the present invention by isomerising the corresponding β-amino-α-benzylidene-propionitrile isomer with a base in a polar aprotic solvent. Under these conditions the 'benzal' is isomerised into the 'benzyl' form, there appearing to be little or no 'benzal' isomer after the process. Suitable aprotic polar solvents and bases are as hereinbefore described with reference to other reactions, and the most preferred solvent is again dimetylsulphoxide and the most convenient bases are the methoxide and t-butoxide anions. Normally there is at least about 0.01, preferably about 0.1 molar concentration of base present in the solvent, and often not more than about 1 molar concentration, though as high as 2 or even 4 molar concentrations may be used. The quantity of solvent is not critical though there is preferably sufficient throughout the isomerisation to dissolve the nitrile. The isomerisation can be effected at room temperature but is most conveniently carried out in the presence of heat, particularly good yields obtained when it is carried out at a temperature above about 20° C. and up to about 75° C. or even higher. The method has been very successfully applied to β-morpholino-α-benzylidene-propionitriles, in particular to those having a 3,4-dimethoxy or 3,4,5-trimethoxy-benzylidene group.

The starting 'benzal' isomer, i.e. the appropriate β-amino-α-benzylidene-propionitrile, for the purposes of the above reaction, can advantageously be prepared by reacting the corresponding benzaldehyde with the corresponding β-aminopropionitrile in an alkanol in the presence of a "catalytic amount" of a base, in the sense hereinbefore used in the present specification, which means an effective quantity of less than 0.3 molar equivalent calculated on the aldehyde reagent.

Alkanols in this reaction are generally lower alkanols, having from 1 to 4 carbon atoms, methanol being particularly preferred. Suitable bases are again those already suggested in connection with base catalysed condensation reactions, but methoxides and tert.-butoxides, particularly the former, are preferred for the present purpose. Best results may be obtained at elevated temperatures, and it is particularly preferred to carry out the reaction at reflux temperatures.

As already indicated, the optimum route for preparing any particular compound according to formula (V) or (VIII) may comprise a combination of a number of the above processing possibilities, depending primarily on the type of amino NR⁵R⁶ group required. For instance, β-primary-anilino-α-3',4',5'-triemthoxy-benzylacrylonitrile has certain especial advantages as an intermediate for the preparation of trimethoprim. Thus, the reaction of guanidine with β-primary-anilino-α-benzylacrylonitriles generally proceeds appreciably faster than that with other β-amino derivatives as defined by formula (V) or (VIII).

The β-anilino-intermediate can moreover be produced readily without any 'benzal' isomer detectable by standard analytical methods, and can be further processed to 2,4-diamino-5-benzylpyrimidines in a very high yield there being little or no polymer formation at all. It is most noteworthy that the reaction with guanidine is readily effected under mild conditions, and both the preparation of the intermediate and the further processing may be completed within hours rather than weeks.

Whilst β-primary-anilino-α-benzylacrylonitriles may be readily prepared by a wide variety of advantageous methods, the choice in any paritcular instance depends partly upon the availability of the starting material, and, for instance, β-anilino-propionitrile, when prepared from aniline and acrylonitrile, usually requires isolation and purification before use. In contrast, the corresponding β-morpholinopropionitrile can be readily formed and need not be isolated. Furthermore, in cases of trimethoxy-substituted benzyl derivatives, and base catalysed reactions, the cheaper and more widely available sodium methoxide is preferred for morpholino-derivatives, whilst the more expensive potassium t-butoxide generally gives best results for anilino-compounds. It may therefore on occasion be advantageous to prepare the morpholino-intermediate first and convert this into the corresponding anilino derivative to obtain optimum results.

According to the present invention in a further aspect there is provided a method of preparing 2,4-diamino-5-benzylpyrimidines as shown in formula IX which are useful as antibacterials, wherein the benzyl group comprises an optionally substituted phenyl group, by reacting the corresponding β-aminio-α-benzylacrylonitrile of formula (V), substantially free from contamination with the β-amino-α-benzylidene-propionitrile isomer, as hereinbefore defined, with guanidine. In particular a method is provided of preparing a compound of formula (IX)

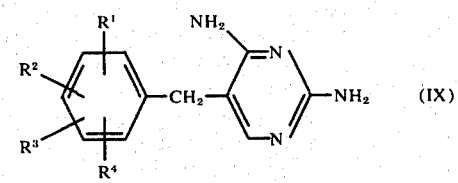

which comprises reacting a compound of formula (VIII) substantially free from contamination with the β-aminio-α-benzylidenepropionitrile isomer, as hereinbefore defined, with guanidine; in formula (IX) $R^1, R^2, R^3$ and $R^4$ are as defined for formula (VIII). It has been found that the pyrimidine products are obtained in a satisfactorily high yield as well as without contamination with polymers and coloured impurities. These aspects are of critical importance as indicated hereinbefore, since contemporary requirements for the purity of pharmaceutical products are very stringent and the products must be manufactured in a very pure form and, of course, at a resonable cost. Both these necessities are now more readily attainable, as a result of the present invention, for the benzylpyrimidines.

To obtain 5-benzylpyrimidines having particularly high activity, or potentiating properties, the para position of the phenyl group is preferably substituted with an alkoxy, i.e. methoxy group, especially in combination with a similar substitution at one or both adjacent meta positions. Such substitutions may also be present when at least one of the ortho-positions is occupied by a lower alkyl group, such as methyl. The pyrimidines are then trimethoprim, diaveridine, ormetoprim and analogues thereof.

For the purposes of obtaining 5-benzylpyrimidines or in particular those of formula (IX) preferably having the above mentioned specific substituents, the appropriate β-anilino-derivatives have been found particularly useful. Advantageously such an amine is reacted with guanidine, conveniently in a lower alcohol solvent, for example, methanol, ethanol, or isopropanol, at elevated temperatures. It is particularly preferred that the reaction is carried out at the reflux temperature of the reaction mixture, but useful routes are found at temperatures down to room temperatures. It has been found specifically that the reaction takes place very readily, taking hours rather than weeks for completion.

Although the reactivity with guanidine, of β-aminio-α-benzylacrylonitriles of formula (V) or (VIII), other than those having a β-primary-anilino group, such as the morpholino derivatives is lower, particularly in alkanols, it has been found that this can be increased and the yield substantially improved if the guanidine is employed in the form of the carbonate in a polar aprotic solvent, as hereinbefore described with reference to other methods, e.g. especially dimethylsulphoxide or hexamethylphosphoramide. Best results have been obtained in these particular cases with dimethylsulphoxide at or near 160° C, and, if the previous reaction step has also been carried out in the same medium the -βamino-α-benzylacrylonitrile intermediate need not be isolated, although isolation is usually preferred since purer benzylpyrimidine is obtained in this manner.

All end products provided in the above manner have either antibacterial activity or potentiating properties, although the degree of such activity and potentiating effect may vary according to substitution and the purpose for which these compounds are employed. Moreover, the products may themselves be used as starting materials to produce other derivatives and analogues by further reactions with functional groups thereon. Thus benzyloxy-benzyl-derivatives may, for instance, be converted into the corresponding hydroxy-benzyl-derivatives by hydrogenation, or any hydroxy-benzyl-derivatives alklated to provide the required alkoxy-benzyl-substituted compounds.

According to the present invention, therefore, there are provided:

i. N=substituted-β-amino-α-benzylacrylonitrile compounds according to formula (V), or, in particular, formula (VIII), substantially free from contamination with β-aminio-α-benzylidenepropionitrile, as hereinbefore described;

ii. the various methods of preparing β-aminio-α-benzylacrylonitriles of formula (V) or (VIII), as hereinbefore described;

iii. the various methods of converting such a β-aminio-α-benzylacrylonitrile into a different compound of the same class with respect of the β-amino-substitution, as hereinbefore described;

iv. N-substituted β-amino-α-benzylacrylonitriles whenever prepared by a method defined under either of paragraphs (ii) and (iii), as hereinbefore described;

v. β-hydroxy-α-benzylacrylonitriles substantially free from contamination with isomers, as hereinbefore described;

vi. the methods of preparing the compounds defined under paragraph (v);

vii. the methods of preparing 5-benzylpyrimidines by using compounds or products of methods, according to any one of paragraphs (i) to (vi), as hereinbefore described;

viii. 5benzylpyrimides whenever prepared by a method including steps according to any one of paragraphs (ii), (iii), (vi) and (vii).

The present invention, in each of the above aspects, is particularly preferred when the phenyl group is a 3,4-dimethoxy, 3,4,5-trimethoxy or 2-methyl-4,5-dimethoxy group, since there are then produced the especially valuable compounds diaveridine, trimethoprim or ormetoprim, or the respective intermediates therefor.

The following Examples illustrate the invention:

EXAMPLES

Example 1

3,4,5 - Trimethoxybenzaldehyde (98g.), β - anilinopropionitrile (85g.), and dimethylsulfoxide (175 ml.) were heated together to 125° C. A solution of sodium methylate (5g.) in methanol (50ml.) was gradually added and in so doing the reaction temperature rose to 130° C, and this temperature was maintained for a further 17 minutes. The reaction mixture was chilled; water was added to a persistent haze; seeds or β-anilino - α -3,4,5 - trimethoxybenzylacrylonitrile were added; and the mixture was stirred at 25° C until precipitation was copious. Additional water (400ml.) was added, and the product was collected by filtration and reslurried in ice water (600ml.). The collection and reslurry procedures were repeated using cold (∼5° C) denatured alcohol (320ml.), and the crystalline β-anilino - α -3,4,5 - trimethoxybenzylacrylonitrile was finally collected; washed with cold denatured alcohol (40ml.), and hexane (100ml.). Wt. =115g. (71%; 98% pure by U.V. assay) m.p. 132° –133° C (recrystallised from methanol).

Example 2

3,4,5-Trimethoxybenzaldehyde (49 g.), βanilinopropionitrile (40 g.), and dimethylsulfoxide (85 ml.) were heated together to 130° C, and a solution of potassium hydroxide (2.5 g.) in methanol (12.5 ml.) was added over a 35 min. period. The temperature of the reaction was maintained at 130°–135° C for an additional 30 min., and the reaction mixture was then treated as in Example 1 to give β-anilino-α-3,4,5-trimethoxybenzylacrylonitrile as a crystalline solid. Wt.=57 g. (70%).

Example 3

3,4,5-Trimethoxybenzaldehyde (117.5 g; 0.6 mole), β-anilinopropionitrile (101 g.; 0.69 mole), and dry distilled dimethylsulfoxide (348 ml.) were heated together to 40° C until solution was complete. The mixture was chilled to 12° C and a solution of potassium t-butoxide in t-butanol (13.6%; 491 ml.; 0.6 mole) was added over the course of about 10 min, such that the final temperature was about 30° C. The temperature was raised to 40° C and maintained for 1 hour. t-Butanol was then stripped from the reaction using vacuum to a final pot temperature of 55° C. The residue was chilled to 30° C and water (100 ml.) and denatured ethanol (50 ml.) added. The mixture was seeded and after obvious crystallisation more ice/water (500 ml.) and denatured ethanol (75 ml.) were added. When the final temperature of the mixture was 5°–10° C the crystalline β-anilino-α-3,4,5-trimethoxybenzylacrylonitrile was collected, and washed with a mixture of cold water/denatured ethanol (85:15; 600 mol.). Wt=181.7 g. (94% pure by U.V. assay; yield 88%).

Example 4

3,4-Dimethoxybenzaldehyde (88 g.) β-anilinopropionitrile (82.5 g.), dimethylsulfoxide (160 ml.), and sodium methylate were heated together at 95° C for 2½hr. The reaction mixture was then chilled to 25° C and diluted with isoproply alcohol (40 ml.) and water. When crystallisation was obvious further water (200 ml.) was added. The mixture was cooled to 5° C and crystalline β-anilino-α-3,4-dimethoxybenzylacrylonitrile was collected and washed with cold water/isopropyl alcohol (1:1) Wt.=99 g. (61%) m.p. 153°–154° C (recrystallised from denatured alcohol).

Example 5

Piperonaldehyde (45 g.), β-anilinopropionitrile (52 g.) and dimethylsulfoxide (96 ml.) were heated together to 120° C and a solution of sodium methylate (2.5 g.) in methanol (12 ml.) was added over a 5 min. period. The temperature was maintained at 115°–120° C for 1 hr. and the mixture was then poured into ice-water. The resulting gum was collected by decantation and was likewise washed with water (2 × 100 ml.). Methanol (100 ml.) was then added and the mixture was heated until solution was complete. Cooling to 5° C gave β-anilino-α-piperonylacrylonitrile as a crystalline solid which was collected, and washed with cold methanol, ether, and pentane. Wt.=45 g. (54%) m.p. 150.5° –151° C (recrystallised from methanol).

Example 5a

The procedure of Example 3 was repeated using 3,4-dimethoxy-5-bromobenzaldehyde (78 g.) and gave β-anilino-α-3,4-dimethoxy-5-bromobenzylonitrile. Wt.=62 g. (52%) m.p. 151°–154° C.

Example 6

Sodium methylate (5.4 g.) in t-butanol (50 ml.) was slowly treated with a solution of 3,4,5-trimethoxybenzaldehyde (20 g.) and β-(p-methylanilino)-propionitrile (17.5 g.) in dimethylsulfoxide (50 ml.). The mixture was stirred at 45° C for 1 hour and the alcohol then removed in vacuo (bath temperature ≯ 50° C). The mixture was poured into ice-water and the crude product collected and recrystallised from methanol to give β-(p-methylanilino)-α-3,4,5-trimethoxybenzylacrylonitrile. Wt.=30 g. (89%) m.p. 150°–151° C (recrystallised from methanol).

Example 7

The procedure of Example 6 was repeated using β-(p-chloroanilino) propionitrile (20 g.) in place of β-(p-methylanilino) propionitrile. Wt. of recrystallised β-(p-chloroanilino)-α-3,4,5-trimethoxybenzylacrylonitrile =]24 g. (67%) m.p. 172°–173° C (recrystallised from methanol).

Example 8

The procedure of Example 6 was repeated using β-(p-methoxyanilino) propionitrile (19.5 g.) in place of β-(p-methylanilino) propionitrile. Wt. of recrystallised β-(p-methoxyanilino)-α-3,4,5-trimethoxybenzylacrylonitrile = 11 g. (33%) m.p. 125°–125° C (recrystallised from methanol).

Example 9

2-Methyl-4,5-dimethoxybenzaldehyde (18 g.), dimethylsulphoxide (35 ml.), sodium methoxide (1.0 g.), and β-anilinopropionitrile were heated together at 95° C for 1½ hr. The mixture was then poured into ice-water (150 g.), and the resulting solid collected by decantation. The crude product was recrystallised from methanol (100 ml.) and the resulting β-anilino-α-(2-methyl-4,5-dimethoxybenzyl) acrylonitrile was collected, and washed with methanol and hexane. Wt. = 19 g. (60%) m.p. 117°–119° C (recrystallised from ethanol/methanol).

Example 10 p-Benzyloxybenzaldehyde (25 g.), β-anilinopropionitrile (22 g.), and dimethylsulphoxide (25 ml.) were heated together to 95° C, and a slurry of sodium methoxide (1 g.) in dimethylsulphoxide (20 ml.) was carefully added such that the temperature rose to 105° C. The mixture was heated to 125°–130° and held at that temperature for 1½ hr. The reaction mixture was poured into ice-water (500 ml.), and the resulting solid was collected and washed by decantation. The crude product was slurried in cold ethanol to give β-anilino-α-(p-benzyloxybenzyl) acrylonitrile. Wt. = 27 g.

Example 11

β-Morpholinopropionitrile (47 g.), sodium methoxide (2 g), and dimethylsulphoxide (40 ml.) were heated together to 65° C, and a solution of 3,4,5-trimethoxybenzaldehyde (50 g.) in dimethylsulphoxide (40 ml.) was added slowly such that the temperature rose to 70°–75° C. After 3 min. at this temperature the mixture was cooled to 30° C, and isopropyl alcohol (30 ml.) and water sufficient to creat a persistent haze were added. The mixture was seeded and, after crystallisation was obvious, water (80 ml.) was added. Crystalline β-morpholino-α-3,4,5-trimethoxybenzylacrylonitrile was collected and washed with isopropyl alcohol (50 ml.). Wt. = 73.5 g. (89%) m.p. 115°–117° C (recrystallised from methanol).

Example 12

3,4,5-Trimethoxybenzaldehyde (20 g.), β-N-methylanilinopropionitrile (18 g.), dimethylsulphoxide (40 ml.), and sodium methoxide (1 g.) were heated together at 110°–115° C for 1.5 hr. The mixture was poured into ice-water (800 ml.) and the crude product which precipitated gave crystalline β-N-methylanilino-α-3,4,5-trimethoxybenzylacrylonitrile after a slurry in methanol (50 ml.). Wt. = 17 g. (50%) m.p. 121°–122° C (recrystallised from methanol.

Example 13

3,4,5-Trimethoxybenzaldehyde (50 g.), β-piperidinopropionitrile (40 g.), di-methylsulphoxide (60 ml.), and sodium methoxide (2 g.) were reacted together at 75° C for 20 min. and on work-up gave β-piperidino-α-3,4,5-trimethoxybenzylacrylonitrile. Wt.=40 g. (50%) m.p. 92°–93° C (recrystallised from methanol).

Example 14

3,4,5-Trimethoxybenzaldehyde (25 g.), β-pyrrolidinopropionitrile (20 g.), dimethylsulphoxide (25 ml.) and sodium methoxide (1 g.) were reacted together at 75° C for 10 min., and on work-up gave β-pyrrolidino-α-3,4,5-trimethoxybenzylacrylonitrile. Wt.=28 g. (75%) m.p. 123°–124° C (recrystallised from methanol).

Example 15

3,4,5-Trimethoxybenzaldehyde (25 g.), β-N-dimethylaminopropionitrile (16 g.), dimethylsulphoxide (45 ml.), and sodium methoxide (1 g.) were reacted together at 70° C for 10 min., and on work-up gave β-dimethylamino-α-3,4,5-trimethoxybenzylacrylonitrile. Wt.=25 g. (73%) m.p. 122°–123° C (recrystallised from methanol).

Example 16

3,4,5-Trimethoxybenzaldehyde (50 g.), β-benzylaminopropionitrile(45 g.), dimethylsulphoxide (80 ml.), and sodium methoxide (2 g.) were heated together at 100° C for 2 hr., and on work-up gave β-benzylamino-α-3,4,5-trimethoxybenzylacrylonitrile. Wt.=32 g. (37%) m.p. 130.5°–131° C (recrystallised from methanol).

Example 17

3,4,5-Trimethoxybenzaldehyde (25 g.), β-morpholinopropionitrile (20 g.), sodium methoxide (2 g.), and N,N-dimethylacetamide (25 ml.) were reacted together at 90°–95° C for 1½ hr., and on work-up gave β-morpholino-α-3,4,5-trimethoxybenzylacrylonitrile. Wt.=15 g. (37%).

Example 18

β-Morpholinopropionitrile (40 g.), dimethylsulphoxide (40 ml.), and sodium methoxide (2 g.) were heated together at 70° C and a solution of 3,4-dimethoxybenzaldehyde (44 g.) in dimethylsulphoxide (40 ml.) was added. The reaction was held at 75°–80° C for 15 min., and then worked-up as in Example 11 to give crystalline β-morpholino-α-3,4-dimethoxybenzylacrylonitrile. Wt.=41 g. (57%) m.p. 130°–131° C (recrystallised from methanol).

Example 19

The procedure of Example 18 was repeated using β-dimethylaminopropionitrile (28 g.) in place of β-morpholinopropionitrile, and on work-up gave β-dimethylamino-α-3,4-dimethoxybenzylacrylonitrile. Wt.=31 g. (50%) m.p. 85°–86° C (recrystallised from methanol).

Example 20

β-Morpholinopropionitrile (20 g.), dimethylsulphoxide (30 ml.), and sodium methoxide (1 g.) were heated together at 80° C and a solution of piperonaldehyde (19 g.) in dimethylsulphoxide was added. The mixture was reacted at 80° C for 15 min., and on work-up gave β-morpholino-α-piperonylacrylonitrile. Wt.=21 g. (61%) m.p. 85°–85.5° C (recrystallised from methanol).

Example 21

The procedure of Example 20 was repeated using 3,4-dimethoxy-5-bromobenzaldehyde (31 g.) in place of piperonaldehyde and on work-up gave β-morpholino-α-3,4-dimethoxy-5-bromobenzylacrylonitrile. Wt.=28 g. (60%) m.p. 94.5°–95° C (recrystallised from denatured ethanol.

Example 22

β-Hydroxy-α-3,4,5-trimethoxybenzylacrylonitrile (132 g.), obtained as hereinafter described in Example 62, was refluxed for 10 min. in benzene containing aniline (50 g.). The solvent was removed by evaporation in vacuo to provide crystalline β-anilino-α-3,4,5-trimethoxybenzylacrylonitrile (165 g.; virtually theoretical yield).

Example 23

A solution of morpholine (10 ml.) and β-hydroxy-α-3,4,5-trimethoxybenzylacrylonitrile (24.9 g.) in ethanol (100 ml.) was refluxed for 30 min. When cooled the reaction gave β-morpholino-α-3,4,5-trimethoxybenzylacrylonitrile. Wt.=27 g. (85%) m.p. 116°–117° C.

Example 24

β-Hydroxy-β-3,4,5-trimethoxyphenethylmethylsulphone (29 g.), β-anilinopropionitrile (16.5 g.), and dimethylsulphoxide (40 ml.) were heated together to 40° C,, and a solution of potassium-t-butoxide in t-butanol (13.6%; 83 ml.) was carefully added. The temperature was maintained at 45° C for 1 hr. Alcohol was then removed from the reaction mixture by vacuum evaporation and the residue was poured into ice-water (200 ml.). The crude crystalline product was collected and recrystallised from ethanol to give β-anilino-β-3,4,5-trimethoxybenzylacrylonitrile. Wt.=26 g. (after washing with ethanol and hexane; 80%).

Example 25

The procedure of Example 24 was repeated using hexamethylphosphoramide (40 ml.) in place of dimethylsulphoxide, and on work-up β-anilino-α-3,4,5-trimethoxybenzylacrylonitrile was obtained. Wt.=26 g. (80%) m.p. 126°–128° C.

Example 26

β-Hydroxy-β-3,4,5-trimethoxyphenethylmethylsulphone (5 g.), β-anilinopropionitrile (3 g.) dimethylsulphoxide (20 ml.), and a solution of potassium hydroxide in methanol (20%; 2 ml.) were reacted together at 90°–95° C for 20 min. Work-up gave β-anilino-α-3,4,5-trimethoxybenzylacrylonitrile (3 g.; 53%). m.p. 126°–129° (recrystallised (recrystalised from ethanol).

Example 27

The procedure of Example 26 was repeated using hexamethylphosphoramide (20 ml.) in place of dimethylsulphoxide and on work-up gave β-anilino-α-3,4,5-trimethoxybenzylacrylonitrile (2 g.; 36%) m.p. 125°–127° C (recrystallised from ethanol).

Example 28

The procedure of Example 26 was repeated using sodium methoxide (0.5 g.) in place of potassium hydroxide in methanol, and on work-up gave β-anilino-α-3,4,5-trimethoxybenzylacrylonitrile. Wt.=3 g. (54%) m.p. 128°–130° C.

Example 29

β-Hydroxy-β-3,4,5-trimethoxyphenethylmethylsulphone (10 g.), β-anilinopropionitrile (5.1 g.), hexamethylphosphoramide (20 ml.), and sodium methoxide (1 g.) were reacted together at 60° C for 30 min., and on work-up gave β-anilino-α-3,4,5-trimethoxybenzylacrylonitrile. Wt.=6 g. (54%) m.p. 127°–129°C.

Example 30

The procedure of Example 28 was repeated using N,N-dimethylacetamide (25 ml.) in place of dimethylsulphoxide, and on work-up gave β-anilino-α-3,4,5-trimethoxybenzylacrylonitrile. Wt.=2.5 g. (45%) m.p. 125°–128° C.

Example 31

β-Hydroxy-β-3,4,5-trimethoxyphenethylmethylsulphoxide (5.4 g.), β-anilinopropionitrile (3 g.), dimethylsulphoxide (25 ml.), and sodium methylate (0.5 g.) were reacted together at 90°–95° C for 1 hr. The mixture was then poured into ice-water; the solid collected; and recrystallised from denatured ethanol to give β-anilino-α-3,4,5-trimethoxybenzylacrylonitrile. Wt.=2 g. (30%) m.p. 125°–127° C.

Example 32

The procedure in Example 31 was repeated using potassium hydroxide (2 g.) in methanol (5 ml.) in place of sodium methoxide, and on work-up gave β-anilino-α-3,4,5-trimethoxybenzylacrylonitrile. Wt.=2 g. (30%) m.p. 125°–128° C.

Example 33

The procedure in Example 31 was repeated using hexamethylphosphoramide in place of dimethylsulphoxide and sodium methylate (2 g.), and on work-up gave β-anilino-α-3,4,5-trimethoxybenzylacrylonitrile. Wt.=2 g. (30%) m.p. 125°–129°C.

Example 34

The procedure in Example 31 was repeated using potassium-t-butoxide in t-butanol (13.6%; 15 ml.) in place of sodium methoxide, and on work-up gave β-anilino-α-3,4,5-trimethoxybenzylacrylonitrile. Wt.=1 g. (15%) m.p. 128°–130° C.

Example 35

The procedure in Example 34 was repeated using hexamethylphosphoramide (25 ml.) in place of dimethylsulphoxide, and on work-up gave β-anilino-α-3,4,5-trimethoxybenzylacrylonitrile. Wt.= 1 g. (15%) m.p. 123°–126° C.

Example 36

β-Morpholinopropionitrile (3.0 g.), β-hydroxy-β-3,4,5-trimethoxyphenethylmethylsulphone (2.9 g.), sodium methoxide (0.3 g.) and hexamethylphosphoramide (6 ml.) were reacted together at 60°–65° C for 40 min., and then poured into ice-water (50 ml.). The crude solid was collected by decantation and recrystallised from ethanol (10 ml.) to give β-morpholino-α-3,4,5-trimethoxybenzylacrylonitrile. Wt.=2 g. (~60%).

Example 37

The procedure in Example 36 was repeated using benzyltrimethylammonium hydroxide in place of sodium methoxide and on work-up β-morpholino-β-3,4,5-trimethoxybenzylacrylonitrile was obtained in 50% yield.

Example 38

3,4,5-Trimethoxybenzaldehyde (40 g.), β-anilinopropionitrile (44 g.), sodium methoxide (32 g.), and methanol were heated together under reflux for 45 min. The reaction mixture was then poured into ice-water (200 ml.) and the resulting thick oil was collected and washed by decantation. Recrystallisation from ethanol gave crystalline β-anilino-α-3,4,5-trimethoxybenzylacrylonitrile. Wt.=42 g. (after washing with ethanol and pentane; 64%).

Example 39

3,4-Dimethoxybenzaldehyde (41.5 g.), β-anilinopropionitrile (38.5 g.), sodium methoxide (40 g.) and methanol (200 ml.) were reacted under reflux for 3 hr. The solvent was then removed by evaporation in vacuo and the resulting paste was recrystallised from methanol to give β-anilino-α-3,4,-dimethoxybenzylacrylonitrile. Wt.=55 g. (75%) m.p. 153°–154° C (recrystallised from ethanol).

Example 40

β-Morpholino-α-3,4,5-trimethoxybenzylacrylonitrile (318 g.), aniline (107 g.) and glacial acetic acid (69 g.) were heated together at 95° C for 45 min. Isopropanol (300 ml.) was then added and the mixture was cooled to 30° C; seeded; and treated with water (300 ml.) after crystallisation was obvious. Filtration gave β-anilino-α-3,4,5-trimethoxybenzylacrylonitrile. Wt.=296 g. (after washing with water and isopropanol; 91%).

Example 41

Aniline hydrochloride, from aniline (10 g.) and conc. hydrochloric acid (12 ml and β-morpholino-α-3,4,5-trimethoxybenzylacrylonitrile (30 g.) were reacted together in refluxing isopropanol (50 ml.) for 15 min. Water (25 ml.) was added and on cooling crystals of β-anilino-α-3,4,5-trimethoxybenzylacrylonitrile were obtained. Wt.=29 g.

Example 42

β-Methoxy-α-3,4,5-trimethoxybenzylidenepropionitrile (53 g.), obtained according to method described in B.P. 957,797, morpholine (100 ml.), sodium methoxide (14 g.), and methanol (53 ml.) were heated together at 90° C for 15 min. The solvent was removed by evaporation in vacuo and the residue was poured into ice-water. The thick oil which separated was collected and washed by decantation and on treatment with ether gave crystalline β-morpholino-α-3,4,5-trimethoxybenzylacrylonitrile. Wt.=53 g. (88%).

Example 43

3,4,5-Trimethoxybenzaldehyde (25 g.), β-morpholinopropionitrile (20 g.), methanol (50 ml.), and sodium methoxide (1 g.) were heated together under reflux for 72 hr. Solvent was then removed in vacuo and the residue was crystallised from diethylether (100 ml.) to give β-morpholino-α-3,4,5-trimethoxybenzylidenepropionitrile. Wt.=18 g. (44%) 100.5°–102° C (recrystallised from methanol).

Example 44

3,4-Dimethoxybenzaldehyde (21 g), β-morpholinopropionitrile (22 g.), sodium methylate (1 g.) and methanol (50 ml.) were heated together under reflux for 20 hr. Work-up as in Example 43 gave β-morpholino-α-3,4-dimethoxybenzylidenepropionitrile. Wt.=25 g. (67%) m.p. 95°–97° C. (recrystallised from methanol).

Example 45

The procedure of Example 43 using β-piperidinopropionitrile (20 g.) gave β-piperidino-α-3,4,5-trimethoxybenzylidenepropionitrile. Wt.=32 g. (79%) m.p. 60°–62° C. (recrystallised from isopropanol).

Example 46

The procedure of Example 43 using β-pyrrolidinopropionitrile (20 g.) gave β-pyrrolidino-α-3,4,5-trimethoxybenzylidenepropionitrile as an oil. Wt.=37 g. (96%).

Example 47

The procedure of Example 43 using β-dimethylaminopropionitrile (18 g.) gave β-dimethylamino-α-3,4,5-trimethoxybenzylidenepropionitrile. Wt.=20 g. (57%) m.p. 81°–83° C (recrystallised from methanol).

Example 48

Piperonaldehyde (30 g.), β-morpholinopropionitrile (40 g.), methanol (75 ml.) and sodium methylate (1.5 g.) were heated together under reflux for 20 hr. Solvent was removed in vacuo and the residue recrystallised from ether, after treatment with aqueous sodium bisulphite, to give β-morpholino-α-piperonylidenepropionitrile. Wt.=29 g. (53%) m.p. 80°–85° C (recrystallised from methanol).

Example 49

β-Morpholino-α-3,4,5-trimethoxybenzylidenepropionitrile (3 g.), dimethylsulphoxide (10 ml.) and sodium methoxide (0.1 g.) were heated together at 50°–60° C for 10 min. Work-up gave crystalline β-morpholino-α-3,4,5-trimethoxybenzylacrylonitrile. m.p. 115°–117° C.

Example 50

The procedure of Example 49 was repeated using β-dimethylamino-α-3,4,5-trimethoxybenzylidenepropionitrile (4 g.) and on work-up gave β-dimethylamino-α-3,4,5-trimethoxybenzylacrylonitrile. Wt.=3.2 g. (80%) m.p. 119°–122° C (recrystallised from methanol).

Example 51

The procedure of Example 49 was repeated using β-piperidino-α-3,4,5-trimethoxybenzylidenepropionitrile (3.5 g.) and in work-up gave β-piperidino-α-3,4,5-trimethoxybenzylacrylonitrile. Wt.=2.7 g. (77%) m.p. 89°–92° C.

Example 52

β-Dimethylamino-α-3,4,5-trimethoxybenzylidenepropionitrile (2 g.), hexamethylphosphoramide (10 ml.), and sodium methoxide (0.05 g.) were heated together at 30° C. Conversion to β-dimethylamino-α-3,4,5-trimethoxybenzylacrylonitrile was complete in 1 min. and this compound was obtained on work-up. Wt.=1 g. (50%) m.p. 118°–120° C (recrystallised from methanol).

Example 53

β-Dimethylamino-α-3,4,5-trimethoxybenzylidenepropionitrile (2 g.), dimethylsulphoxide (10 ml.) and potassium-t-butoxide (0.05 g.) at 30° for 1 min. gave β-dimethylamino-α-3,4,5-trimethoxybenzylacrylonitrile. Wt.=1 g. (50%) m.p. 119°–121°C.

Example 54

β-Dimethylamino-α-3,4,5-trimethoxybenzylidenepropionitrile (4 g.), hexamethylphosphoramide (10 ml.) and potassium-t-butoxide (0.05 g.) at 30° C for 1–2 min. gave β-dimethylamino-α-3,4,5-trimethoxybenzylacrylonitrile. Wt.= 3 g. (75%) m.p. 117°–119° C.

Example 55

β-Dimethylamino-α-3,4,5-trimethoxybenzylidenepropionitrile (2 g.), dimethylsulphoxide (10 ml.), and 3 drops of a saturated solution of potassium hydroxide in methanol at 40° C for 5 min. gave β-dimethylamino-α-3,4,5-trimethoxybenzylacrylonitrile Wt.=1.3 g. (65%) m.p. 118°–120°C.

Example 56

The procedure as in Example 55 using hexamethylphosphoramide in place of dimethylsulphoxide in 2 min. gave β-dimethylamino-α-3,4,5-trimethoxybenzylacrylonitrile Wt.=1.8 g. (90%) m.p. 121°–123° C.

Example 57

The procedure as in Example 49 using β-pyrrolidino-α-3,4,5-trimethoxybenzylidenepropionitrile gave β-pyrrolidino-α-3,4,5-trimethoxybenzylacrylonitrile. m.p. 123°–124° C.

Example 58

The procedure as in Example 52 using β-morpholino-α-3,4,-dimethoxybenzylidene propionitrile gave β-morpholino-α-3,4-dimethoxyacrylonitrile. m.p. 127°–129° C.

Example 59

The procedure as in Example 49 using β-morpholino-α-piperonylidenepropionitrile (5.0 g.) gave β-morpholino-α-piperonylacrylonitrile. Wt.=4.5 g. (90%) m.p. 82°–84° C.

Example 60

The procedure as in Example 50 using N,N-dimethylacetamide in place of dimethylsulphoxide gave β-dimethylamino-α-3,4,5-trimethoxybenzylacrylonitrile in 83% yield. m.p. 121°–123° C.

Example 61

The procedure as in Example 52 using benzyltrimethylammonium hydroxide in place of sodium methoxide gave β-dimethylamino-α-3,4,5-trimethoxybenzylacrylonitrile in 86% yield. m.p. 122°–123° C.

Example 62

β-Morpholino-α-3,4,5-trimethoxybenzylacrylonitrile (157 g.) was treated with conc. hydrochloric acid (75 ml.) in water (180 ml.) at 60° C for 15 min. The reaction mixture was cooled, extracted with chloroform (100 ml.; 75 ml.; 75 ml.), and the extracts were backwashed with water (75 ml.). Removal of solvent gave β-hydroxy-α-3,4,5-trimethoxybenzylacrylonitrile as a thick oil. Wt.=125 g. (theory).

Example 63

β-Hydroxy-α-3,4,5-trimethoxybenzylacrylonitrile (70 g.) in methanol (150 ml.) at 10° C was treated with dimethylsulphate (39 g.). To the mixture was then gradually added a solution of potassium hydroxide (20 g.) in methanol (30 ml.) and water (12 ml.) and the reaction was then kept at 10° C for 15 min. The mixture was next heated to 60° C for 15 min.; then cooled; and finally solvent was removed to a residue which was slurried in water (100 ml.) and extracted into chloroform (2 × 80 ml.). The chloroform extract, after backwashing with water (70 ml.), drying, and treatment with charcoal, was evaporated to dryness to give β-methoxy-α-3,4,5-trimethoxybenzylacrylonitrile. Wt.=61 g. (80%).

Example 64

β-Anilino-α-3,4,5-trimethoxybenzylacrylonitrile (32 g.) and a solution of guanidine hydrochloride (19 g.) and sodium methoxide (13 g.) in denatured ethanol (100 ml.) were heated under reflux for 2½ hr. Solvent (31 ml.) was boiled off and the mixture was cooled to 5° C. The resulting crystals of 2,4-diamino-5-(3',4',5'-trimethoxybenzyl)pyrimidine were collected and washed with denatured ethanol and acetone. Wt.=27 (94%) m.p. 198°–200° C.

Using methanol in place of denatured alchohol gave 2,4-diamino-5-(3',4', 5'-trimethoxybenzyl)pyrimidine in 86% yield after 6 hr. reflux; with isopropanol the reaction was over in 2 hrs. and the yield was 78%.

Example 65

The product from Example 6 was converted to 2,4-diamino-5-(3',4',5'-trimethoxybenzyl)pyrimidine by the procedure of Example 64 in 2 hr. Yield=90%.

Example 66

The product from Example 7 was converted to 2,4-diamino-5-(3',4',5'-trimethoxybenzyl)pyrimidine by the procedure of Example 64 in 2 hr. Yield=90%.

Example 67

The product from Example 8 was converted to 2,4-diamino-5-(3',4',5'-trimethoxybenzyl)pyrimidine by the procedure of Example 64 in 4½ hr. Yield=90%.

Example 68

The procedure of Example 64 was repeated using β-anilino-α-3,4-dimethoxybenzylacrylonitrile (29.4 g.) and gave 2,4-diamino-5-(3',4'-dimethoxybenzyl)pyrimidine. Wt.=25.5 g. (98%) m.p. 230°–233° C.

Example 69

The procedure of Example 64 was repeated using β-anilino-α-piperonylacrylonitrile (28 g.) and gave 2,4-diamino-5-piperonylpyrimidine. Wt.=22 g. (89.5%) m.p. 252°–253° C (recrystallised from denatured alcohol).

Example 70

The procedure of Example 64 was repeated using β-anilino-α-2-methyl-4,5-dimethoxybenzylacrylonitrile (16 g.) and after 18–20 hr. reflux gave 2,4-diamino-5-(2'-methyl-4',5'-dimethoxybenzyl)pyrimidine. Wt.=11.5 g. (92%) m.p. 230°–231° C.

Example 71

The procedure of Example 64 was repeated using β-anilino-α-3,4-dimethoxy-5-bromobenzylacrylonitrile (62 g.) and gave 2,4-diamino-5-(3',4'-dimethoxy-5'-bromo-benzyl)pyrimidine. Wt.=38 g. (70%) m.p. 203.5°–205° C.

Example 72

The procedure of Example 64 was repeated using β-anilino-α-p-benzyloxybenzylacrylonitrile (25 g.) and gave after 4 hr. reflux 2,4-diamino-5-(p-benzyloxybenzyl)pyrimidine. Wt.=20.5 g.. This was converted to its acetate salt by treatment with acetic acid. Wt.=15 g.

Example 73

2,4-Diamino-5-(p-benzyloxybenzyl)pyrimidine acetate (4.6 g.) in methanol (200 ml.) was hydrogenated at low pressure over 5% Palladium/Carbon. The filtrate after removal of catalyst was evaporated and the resulting residue purified by dissolution in hot dilute acetic acid and re-precipitation with ammonium hydroxide to pH 9. Crystalline 2,4-diamino-5-(p-hydroxybenzyl)-pyrimidine was collected and washed with water. Wt.=2.16 g. m.p. 300°–303° C.

Example 74

β-Morpholino-α-3,4,5-trimethoxybenzylacrylonitrile (32 g.), guanidine carbonate (34 g.) and dimethylsulphoxide (50 ml.) were heated together at 160° C for 1 hr. with good stirring. The reaction mixture was cooled and poured into ice-water (200 ml) and gave 2,4-diamino-5-(3',4',5'-trimethoxybenzyl)pyrimidine which was collected and washed with water and acetone. Wt.=23.6 g (80%) m.p. 196°–198° C.

Example 75

The procedure of Example 74 was repeated using β-N-methylanilino-α-3,4,5-trimethoxybenzylacrylonitrile and gave 2,4-diamino-5-(3',4',5'-trimethoxybenzyl)pyrimidine.

Example 76

The procedure of Example 74 was repeated using β-piperidino-α-3,4,5-trimethoxybenzylacrylonitrile and gave 2,4-diamino-5-(3',4',5'-trimethoxybenzyl)-pyrimidine.

Example 77

The procedure of Example 74 was repeated using β-pyrrolidino-α-3,4,5-trimethoxybenzylacrylonitrile and gave 2,4-diamino-5-(3',4',5'-trimethoxybenzyl)-pyrimidine.

Example 78

The procedure of Example 74 was repeated using β-dimethylamino-α-3,4,5-trimethoxybenzylacrylonitrile and gave 2,4-diamino-5-(3',4',5'-trimethoxybenzyl)pyrimidine.

Example 79

The procedure of Example 74 was repeated using β-benzylamino-α-3,4,5-trimethoxybenzylacrylonitrile and gave 2,4-diamino-5-(3',4',5'-trimethoxybenzyl)-pyrimidine.

Example 80

The procedure of Example 74 was repeated using β-morpholino-α-3,4-dimethoxybenzylacrylonitrile and gave 2,4-diamino-5-(3',4'-dimethoxybenzyl)pyrimidine.

Example 81

The procedure of Example 74 was repeated using β-dimethylamino-α-3,4-dimethoxybenzylacrylonitrile and gave 2,4-diamino-5-(3',4'-dimethoxybenzyl)-pyrimidine.

Exammple 82

The procedure of Example 74 was repeated using β-morpholino-α-piperonylacrylonitrile and gave 2,4-diamino-5-piperonylpyrimidine.

Example 83

The procedure of Example 74 was repeated using β-morpholino-α-3,4,-dimethoxy-5-bromobenzyla-crylonitrile and gave 2,4-diamino-5-(3',4'-dimethoxy-5'-bromobenzyl) pyrimidine.

Example 84

The procedure of Example 64 was repeated using β-methoxy-α-3,4,5-trimethoxybenzylacrylonitrile (54 g.) and after 20 hr. reflux gave 2,4-diamino-5-(3',4',5'-trimethoxybenzyl)pyrimidine. Wt.=56 g. (94%) m.p. 198°-200° C.

Example 85

Under the conditions of Ex. 24 the β-hydroxy-β-(3,4-dichlorophenethylmethylsulfone, β-hydroxy-β(o, meta, p-iodophenyl)methylsulfones and β-hydroxy-β-(o-bromophenethylsulfones) were condensed with β-anilinopropionitrile to yield the corresponding β-anilino-α-halogenobenzylacrylonitriles.

Example 86

The procedure of example 64 was repeated using the products of ex. 85 to give 2,4-diamino-5=(3',4'-dichlorobenzyl) pyrimidine, m.p. 237°-239°, 2,4-diamino-5-(o-iodobenzyl) pyrimidine, m.p. 265°-267°, 2,4-diamino-5-(m-iodobenzyl) pyrimidine, m.p. 220.5 -222°, 2,4-diamino-5-(p-iodobenzyl) pyrimidine, m.p. 246°-248°, and 2,4-diamino-5-(o-bromobenzyl) pyrimidine, m.p. 248°-250°.

Example 87

β-hydroxy-α-3,4,5-trimethoxy-benzylacrylonitrile 25 grams, denatured ethanol (70 ml.) 2,4-dimethyl aniline (14 ml.) refluxed together for 1 hr. Solvent removed by evaporation and vacuumed and the residue was poured into ice water. The resulting thick gum was collected and recrystallized from methanol to give crystaline β-2,4-dimethylanidino -α-3,4,5-trimethoxybenzyla-crylonitrile. Wt.=11g. (31% yield) M.P. 123°-125° C.

Example 88

Procedure of Example 87 was repeated using 3,4,5-trimethoxyaniline and gave β-3,4,5-trimethoxybenzyla-crylonitrile in 65% yield. M.P. 156°-161° C. Recrystallized from denatured ethanol.

Example 89

Procedure of Example 87 was repeated using 2,5-dichloroaniline and gave β-2,5,-dichloroanilino-α-3,4,5-trimethoxybenzylacrylonitrile. 20 g, 51% yield. A sample recrystallized from denatured ethanol melted at 130° C, resolidified, and then remelted at 150° C.

Example 90

Procedure of Example 87 was repeated using α-naphthylamine 14.3gr. and gave crystaline β-1-naphthylamino -α-3,4,5-trimethoxybenzylacrylonitrile. Wt.=26 gr. 70% yield, melting pt. 107°-109° C.

Example 91

The product from Example 87 was converted to trimethoprim by the procedure of Example 64 in 4 hrs. Yield 92%.

Example 92

The product from Example 88 was converted to trimethoprim by the procedure of Example 64 in 3 hrs. Yield above 90%.

Example 93

The product from Example 89 was converted to trimethoprim by the procedure of Example 64 in 1.5 hrs. Yield 95%. This reaction was repeated as in Example 64 except at room temperature and useful yield of trimethoprim was obtained in several hrs.

Example 94

The product from Example 90 was converted to trimethoprim by the procedure of Example 64 in several hrs. Yield 72%.

Example 95

Methylα-(3,4,5-trimethoxyacetophenone) Sulphone

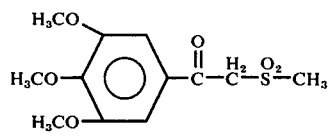

Charge into a 500 ml. three necked flask equipped with stirrer and reflux condenser, 27 gms. (0.69M) sodium amide, 225 ml. dimethylsulphoxide and 56.5 gm. dimethylsulphone (0.6M). Heat to 55° C for 1 hour with stirring, and cool to 50° C. Add 65.4 gm. (0.20M) 3,4,5-trimethoxymethylbenzoate and heat to 60° C for 1 hour to complete the reaction.

Pour the mixture onto 1100 gm. of ice and acidify with 180 ml. dilute HCl (1:1). Cool in an ice bath and filter the crystalline product. Wash with 2×150 ml. of ice water and 2×100 ml. ice cold lower alcohol such as ethanol. Air dry overnight or vacuum dry at 40° C to constant weight. The yield will be 74 gm. or 88% of theory of suitable intermediate for the next step. A.N. Sample M.P. 147°-148° C Recrystallized from Ethanol

|   | Calculated | Found |
|---|---|---|
| C | 49.98 | 49.8 |
| H | 5.59 | 5.54 |

Example 96

Reduction of methyl α(3,4,5-trimethoxyacetophenone) sulphone to the corresponding alchohol

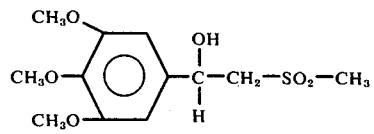

Set up a 3 neck 1 liter flask equipped with a stirrer in an ice bath. Charge with 38.1 gm. of methyl α(3,4,5-trimethoxyacetophenone) sulphone, 100 ml. desalted water and 30 ml. ethanol and cool this slurry to +15° C. Add portion wise a precooled solution of 2 gm. sodium borohydride in 40 ml. desalted water. The first few ml. will cause a slight foaming but it can be controlled easily with a few ml. of ethanol. Additional ethanol can be used to wash down the sides of the reaction flask.

At the end of the addition of the borohydride remove the cooling bath and stir for 1 hour. Completion of the reaction is checked by U.V. Cool the slurry to +2° C and filter all solids. Wash with small amounts of ice water and dry in vacuum oven at 50° C to constant weight. The yield will be 34.2 gm. or 89.3% of theory. A.N. Sample M.P. 153°–154° C Recrystallized from ethanol

|   | Calculated | Found |
|---|---|---|
| C | 49.7 | 49.39 |
| H | 6.24 | 6.27 |

Example 97

ω-(Methylsulfinyl)3,4,5-Trimethoxyacetophenone

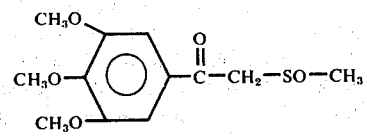

Into a three necked flask, equipped with condenser, stirrer and thermometer, charge 4.0 gm. sodium amide (hexane washed) and 75 ml. dimethyl sulphoxide (distilled and dried). Slowly warm (in an external water bath) to 45° C and the reaction begins. Raise temperature gradually to 60° C and maintain for 1 hour, to complete.

Cool to +15° and add dropwise a solution of 12 gm. 3,4,5-trimethoxymethylbenzoate in 25 ml. of dimethylsulphoxide. Keep the temperature between 20°–25° C by external cooling. Stir ½ hour at room temperature and quench into 300 ml. ice water. Carefully acidify to pH 5–6 with cold dilute hydrochloric acid.

Extract into chloroform 3×100 ml. wash the organic layer with 4×50 ml. water, dry over sodium sulphate, filter and flash evaporate all solvent.

The heavy oil will weigh 15 gm. and slowly crystallize on standing.

To purify; dissolve the thick oil in 75 ml. ethyl acetate, charcoal and cool the filtrate in an ice acetone bath. Filter and dry the white solid. Wt. = 10 gm. ≈70% yield. M.P. 113°–115° C.

A.N. Sample M.P. 115°–116° C Recrystallized from acetone

|   | Calculated | Found |
|---|---|---|
| C | 53.05 | 52.69 |
| H | 5.92 | 5.84 |

Example 98

β-Hydroxy β-3,4,5-trimethoxyphenethylmethylsulphoxide

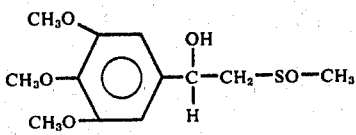

Combine 14 gm.ω(methylsulfinyl)3,4,5-trimethoxyacetophenone, 50 ml. desalted water and 35 ml. methanol. Cool to +15° C and with magnetic stirring add slowly a solution of 0.5 gm. sodium borohydride in 10 ml. water. The reaction is exothermic but can be controlled between 15°–20° C with external cooling.

Stir at room temperature for 2 hours, check for completion by U.V. and finally strip off methanol by vacuum at 45°–50° C.

Extract the aqueous solution with 3×75 ml. chloroform, wash with the organic layer 1×75 ml. water, dry over magnesium sulphate, filter and evaporate to a clear thick oil. A few drops of ethyl acetate causes complete crystallization. Weight = 14 gm. This is suitable for use in the next step without further purification.

A.N. Sample P. 150°–155° C (Isomers) Recrystallized from Ethyl Acetate.

|   | Calculated | Found |
|---|---|---|
| C | 52.4 | 52.37 |
| H | 6.61 | 6.70 |

Example 99

α(3,4,5-Trimethoxybenzyl) β-anilinoacrylonitrile

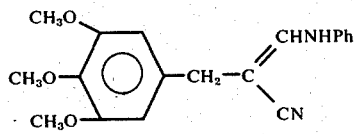

Combine in a flask at room temperature 5.4 gm. β-hydroxy-β-3,4,5-trimethoxyphenethyl methyl sulphoxide, 3 gm. β-anilinopropionitrile, 25 ml. dimethylsulphoxide and 2.0 gm. sodium methylate. Warm slowly with stirring, on a steam bath up to 90°–95° C. It gets very dark in color. Reaction, by U.V., is complete in 20 minutes at 95° C.

Quench in ice water and wash the dark oily precipitate by decantation. Dissolve in 15 ml. of ethanol and cool. Filter the heavy yellow crystalline precipitate, wash with cold ethanol and hexane. Dry. Wt. = 2 gm. ≈31% yield. The U.V., I.R., and M.P. are identical to that prepared from the 3,4,5-trimethoxybenzaldehyde and β-anilinopropionitrile. Ph = phenyl.

Example 100

α(3,4,5-trimethoxybenzyl)-β-anilinoacrylonitrile

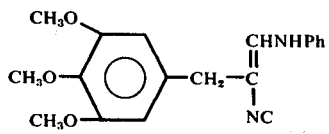

In a three neck flask equipped with stirrer, condenser and thermometer, charge 29 gm. β-hydroxy-β-3,4,5-trimethoxyphenethylmethylsulphone, 16.5 gm. β-anilinopropionitrile and 40 ml. dimethylsulphoxide. Warm to 40° C with stirring, and gradually add 83 ml. of a 13.6% solution of potassium tertiary butoxide in tertiary butanol. Maintain internal temperature at 45° C for 1 hour and check for completion by U.V.

Strip as much alcohol as possible by vacuum using an external water bath (70° C) and quench in ice water (200 ml.). Stir until the thick oil turns crystalline an filter. Wash the cake with ice water and finally hexane. Vacuum dry at 35° C to constant weight. The yield will be 32 gm.* or theory of crude α-(3,4,5-trimethoxybenzyl-β-anilinoacrylonitrile). The U.V. is satisfactory and it may be used directly in the preparation of Trimethoprim.

* Recrystallisation Dissolve the crude intermediate in 75 ml. hot ethanol. Cool in ice/acetone bath (preferably overnight) and filter. Wash the cake with cold ethanol (15 ml.) and hexane. Vacuum dry. Weight = 26+gm.≈80% yield.

Example 101

Trimethoprim 2,4-diamino-5-(3',4',5'-trimethoxybenzyl) pyrimidine

Prepare a guanidine solution from 15 gm. guanidine HCl, 10 gm. sodium methylate, and 100 ml. ethanol. Cool, filter salt free, and combine with 16 gm. α(3,4,5-trimethoxybenzyl)β-anilinoacrylonitrile. Reflux in a steam bath overnight, charcoal the hot solution with 2.0 gm. Darco G-60 and evaporate to ¼ volume. Cool to complete crystallization, filter, and wash with cold ethanol, acetone, and ether. Dry. Weight = 13+gm.~91% theory. M.P. 198°–200° C.

Example 102

β-Hydroxy β-3,4,5-trimethoxyphenethylmethylsulphoxide

Sodium methylate (5.4 gm.) was dissolved in hot dimethylsulfoxide (50 ml.), the solution was cooled to room temperature, 3,4,5-trimethoxybenzaldehyde (18 gm.) was added, and the mixture was stirred at room temperature for 2 hours. Water (100 ml.) was then added to the mixture which was next extracted with chloroform. The chloroform extract was washed with water, dried over anhydrus sodium sulfate, and evaporated to dryness. The residual yellow oil crystallised on addition of ethylacetate. The crystals were collected and washed with pentane. Wt. = 14.8 gm. (59%) M.P. 160°–162° C (After recrystallisation from ethylacetate.) I.R. and U.V. spectra in agreement with structure.

|   | Calculated | Found |
|---|---|---|
| C | 52.4 | 52.37 |
| H | 6.61 | 6.70 |

What we claim is:

1. The method of preparing a compound of the formula

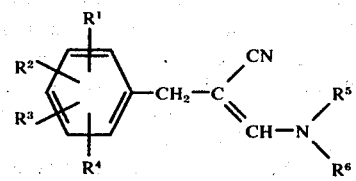

which comprises reacting

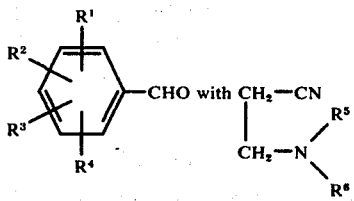

wherein $R^1$–$R^4$ are the same or different and each is hydrogen, halogen, lower alkyl, lower alkoxy, or benzyloxy, or $R^3$ and $R^4$ taken together is methylenedioxy when both $R^1$ and $R^2$ are hydrogen in the presence of a base selected from the group consisting of hydroxides, alkoxides and methylsulphinyl carbanion in association with an alkali metal or quaternary ammonium cation in a polar aprotic solvent compatible with and dissolving both reactants, wherein $NR^5R^6$ is selected from the group consisting of anilino, N-methyl anilino, N-ethyl anilino where the phenyl ring thereof is substituted by one or more halogen, alkyl or alkoxy, monoalkylamino, benzylamino, α-naphthylamino, β-naphthylamino, pyrrolidino, piperdino, piperazino and morpholino and wherein the said $NR^5R^6$ group has not more than 12 carbon atoms and can have only one hydrogen atom for $R^5$ and $R^6$.

2. The method according to claim 1 in which the base ranges in amount from about .3 to about 2 molar equivalents.

3. The method according to claim 2 in which the base is lower alkoxide anion.

4. The method according to claim 3 in which the alkoxide anion is methoxide.

5. The method according to claim 1 in which $R^5$ is hydrogen, $R^6$ is phenyl, one of $R^1$–$R^4$ is hydrogen and the others are methoxy at the 3,4 and 5 positions of the ring.

6. The method according to claim 1 in which the nitrile is β-morpholino-propionitrile.

7. The method of claim 1 in which the nitrile is β-morpholino-propionitrile.

8. The method of claim 1 in which the nitrile is β-anilinopropionitrile.

9. The method of claim 1 in which the nitrile is β-piperidinopropionitrile.

10. The method of claim 1 in which the nitrile is β-pyrrolidinopropionitrile.

* * * * *